(12) United States Patent
Sioshansi et al.

(10) Patent No.: US 8,182,410 B2
(45) Date of Patent: May 22, 2012

(54) PERIPHERAL RADIOTHERAPY OF PROTRUDING CONFORMABLE ORGANS

(75) Inventors: Piran Sioshansi, Lincoln, MA (US); Raymond J. Bricault, West Boylston, MA (US)

(73) Assignee: Advanced Radiation Therapy, LLC, Billerica, MA (US)

( * ) Notice: Subject to any disclaimer, the term of this patent is extended or adjusted under 35 U.S.C. 154(b) by 1592 days.

(21) Appl. No.: 11/354,620

(22) Filed: Feb. 15, 2006

(65) Prior Publication Data

US 2006/0183960 A1  Aug. 17, 2006

Related U.S. Application Data

(60) Provisional application No. 60/653,191, filed on Feb. 15, 2005.

(51) Int. Cl.
*A61N 5/00* (2006.01)
(52) U.S. Cl. .......................................................... 600/1
(58) Field of Classification Search .................. 600/1–8; 378/65; 250/506.1
See application file for complete search history.

(56) References Cited

U.S. PATENT DOCUMENTS

| | | | |
|---|---|---|---|
| 4,780,898 A | 10/1988 | Sundqvist | 378/65 |
| 5,528,651 A | 6/1996 | Leksell et al. | 378/65 |
| 5,540,737 A | 7/1996 | Fenn | |
| 5,629,967 A | 5/1997 | Leksell et al. | 378/65 |
| 6,049,587 A | 4/2000 | Leksell et al. | 378/65 |
| 6,560,312 B2 | 5/2003 | Cash | 378/65 |
| 6,574,499 B1 | 6/2003 | Dines et al. | |
| 6,768,925 B2 | 7/2004 | Fenn et al. | |
| 7,492,858 B2 * | 2/2009 | Partain et al. | 378/37 |
| 2002/0006182 A1 | 1/2002 | Kim et al. | |
| 2004/0245483 A1 | 12/2004 | Smit et al. | |
| 2005/0254620 A1 * | 11/2005 | Shoji et al. | 378/37 |
| 2006/0224035 A1 | 10/2006 | Russell et al. | |

FOREIGN PATENT DOCUMENTS

WO  WO 01/89379 A1  11/2001

OTHER PUBLICATIONS

International Search Report and the Written Opinion from Corresponding Application No. PCT/US06/005212 dated Jun. 13, 2008.
European Office Action dated Sep. 7, 2010.

* cited by examiner

*Primary Examiner* — Charles A Marmor, II
*Assistant Examiner* — Christine Hopkins
(74) *Attorney, Agent, or Firm* — McDermott Will & Emery LLP

(57) ABSTRACT

A system for and method of applying non-invasive brachytherapy to a targeted volume within a protruding organ of a patient, employs an applicator constructed so as to be positioned relative to the organ so that an enhanced dose of divergent radiation is deliverable from at least two locations at or very near the periphery of the organ transcutaneously to the targeted volume of the protruding organ from at least two directions so that a higher dose is delivered to the targeted volume than to tissue surrounding the targeted volume. The treatment planning, and image guidance techniques are also described.

19 Claims, 16 Drawing Sheets

PERIPHERAL RADIOTHERAPY OF PROTRUDING CONFORMABLE ORGANS

RELATED APPLICATION

The present application is based upon and claims priority from U.S. Provisional Application Ser. No. 60/653,191, entitled Peripheral Brachytherapy of Protruding Organs Using Distributive Radioactive Sources, and filed in the names of Raymond J. Bricault and Piran Sioshansi on Feb. 15, 2005. This application is being filed contemporaneously with related application, U.S. Ser. No. 11/354,614, entitled Peripheral Brachytherapy of Protruding Organs Using Distributive Radioactive Sources, and filed in the names of Raymond J. Bricault and Piran Sioshansi on Feb. 15, 2006.

FIELD OF DISCLOSURE

The disclosure generally relates to brachytherapy, and more specifically to non-invasive devices for and methods of providing peripheral brachytherapy to protruding organs.

BACKGROUND OF THE DISCLOSURE

Various forms of brachytherapy have been practiced since the time of discovery of radioactivity by Mme. Curie. Brachytherapy, from the Greek root meaning "from a short or near distance" is a term typically used to describe the placement of one or more radioactive sources within tissue or in a body lumen or body cavity to deliver a therapeutic dose to a tumor or tumor bed near the source. Brachytherapy as it is practiced today includes several varieties of invasive treatment. Interstitial brachytherapy includes the step of placing the radioactive source or sources within the tissue (e.g. prostate gland). Intra-luminal brachytherapy includes introducing the source through an anatomical lumen (e.g. vascular). Intra-cavitary brachytherapy is performed by placing the radioactive source inside a naturally occurring cavity near the cancerous tissue (e.g. cervical cancer, or orbital cavity for intra-ocular melanoma), or a man-made cavity created during surgery (e.g. breast lumpectomy or other tumor beds). Various brachytherapy applicators are known and used in invasive procedures.

A surface applicator, including structure for defining a series of parallel lumens for receiving high dose radiation (HDR) sources, has been used for treatment of surface lesions, skin cancer or during open surgeries for tissues which are easily accessed. (See, for example, the Varian catalog at www.varian.com/obry/pdf/vbtapplicatorcatalogue.pdf, page 113). This applicator is not designed to treat a deep seated tumor or tumor bed, however.

Cash et al. (U.S. Pat. No. 6,560,312) discloses a technique of performing radiosurgery on a human body using teletherapy. The technique includes accumulating non-converging radiation fields to reach a therapeutic dose. The teletherapy design of Cash et al. is based upon a predetermined distribution of remote x-ray sources to create a volume where multiple beams intersect within the human body. It relies on the ability to align remote sources located on one platform to treat a lesion within a patient who is positioned on a separate platform. This approach has major limitations where relative positioning of the sources must be carefully maintained in order to provide precise lesion tracking, particularly when patient motion, such as that associated with breathing, can cause misalignments during treatment (as for example, when the patient is being treated for breast cancer).

Sundqvist (U.S. Pat. No. 4,780,898) and Leskell (U.S. Pat. Nos. 5,528,651, 5,629,967 and 6,049,587) collectively describe a teletherapy system sold under the trademark "GammaKnife", and assigned to Elekta Instrument AB. The system is used to treat inoperable fine brain tumors by exposing a localized point within the brain of the patient. Gamma Knife relies on rigidly immobilizing the head of a patient by attaching a "helmet" directly to the skull, and simultaneously exposing the brain tissue to sources of radiation from multiple angles. Each source is collimated, emitting converging radiation beamlets that target a single focus point. By careful alignment of each of the source beamlets or lines of treatment, the Gamma-Knife system is able to build up the radiation field to therapeutic levels at the location of the target. The design is useful for treatment of very fine (point) lesions and requires careful orientation of each beamlet or line of treatment.

GENERAL DESCRIPTION OF THE DRAWINGS

Figure 9A:
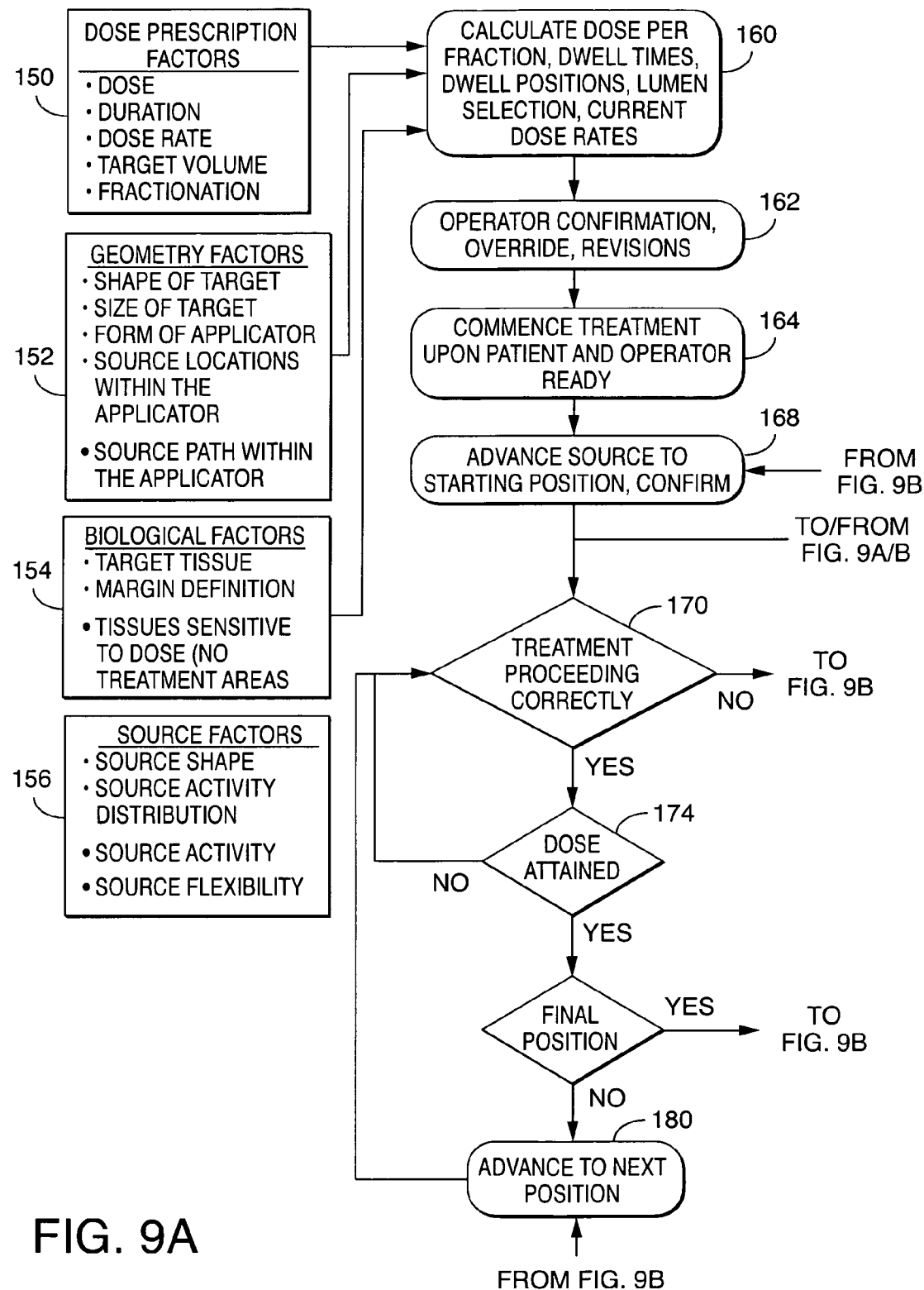
Figure 10:
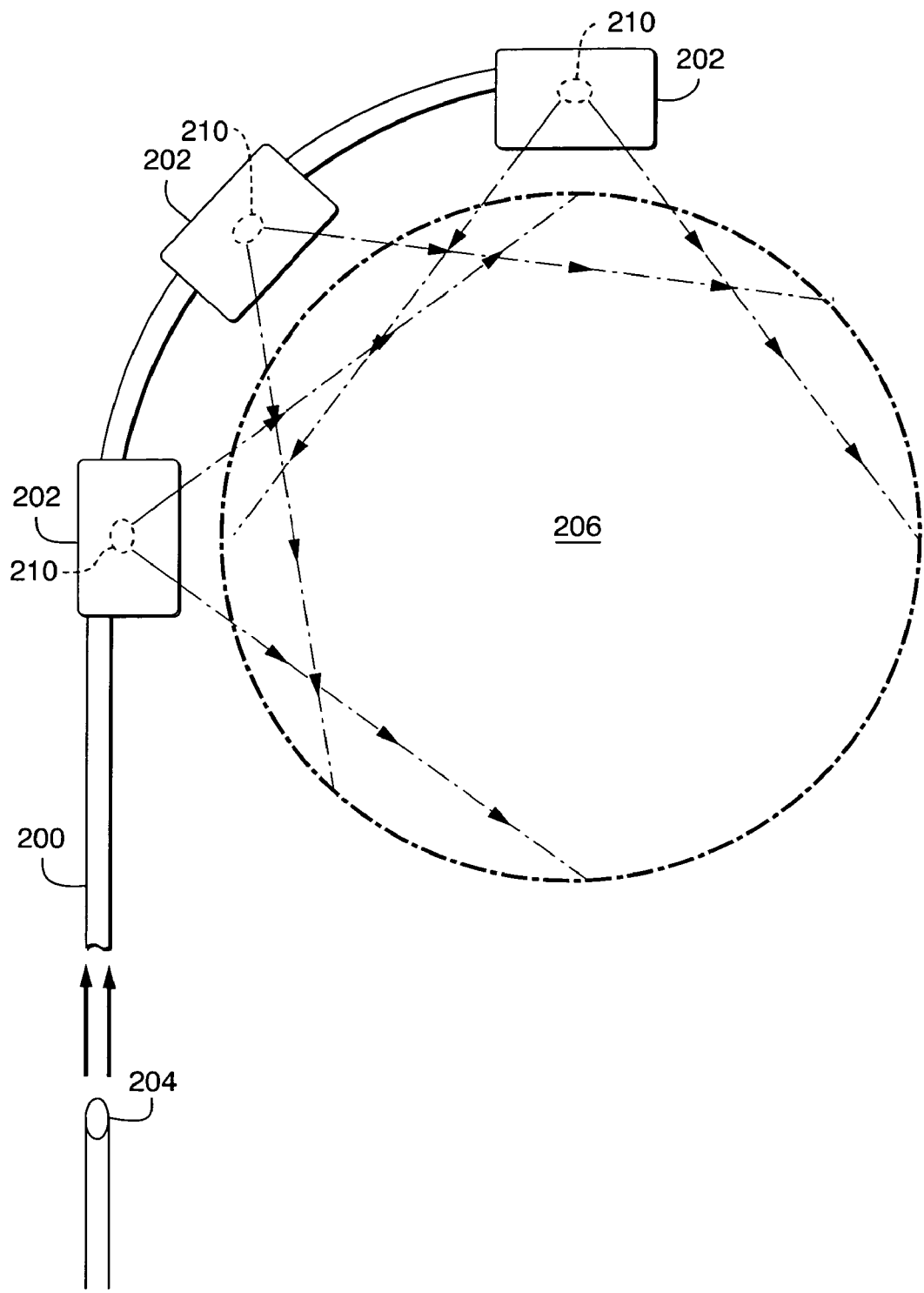
Figure 11A:
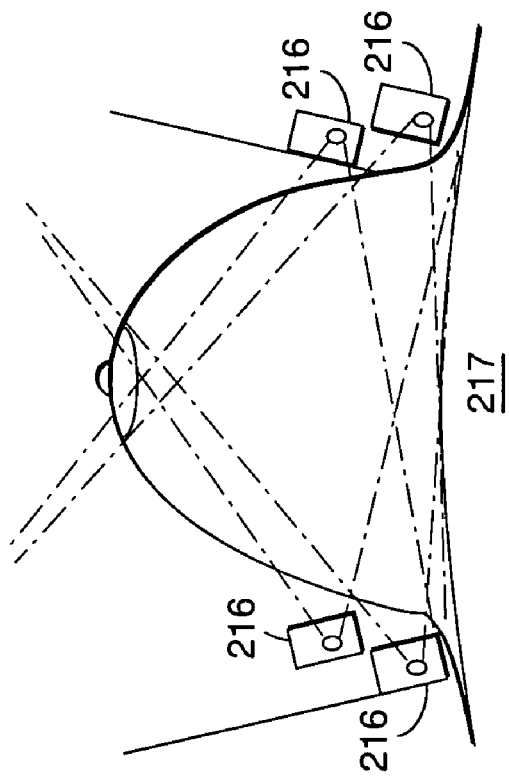
Figure 12:
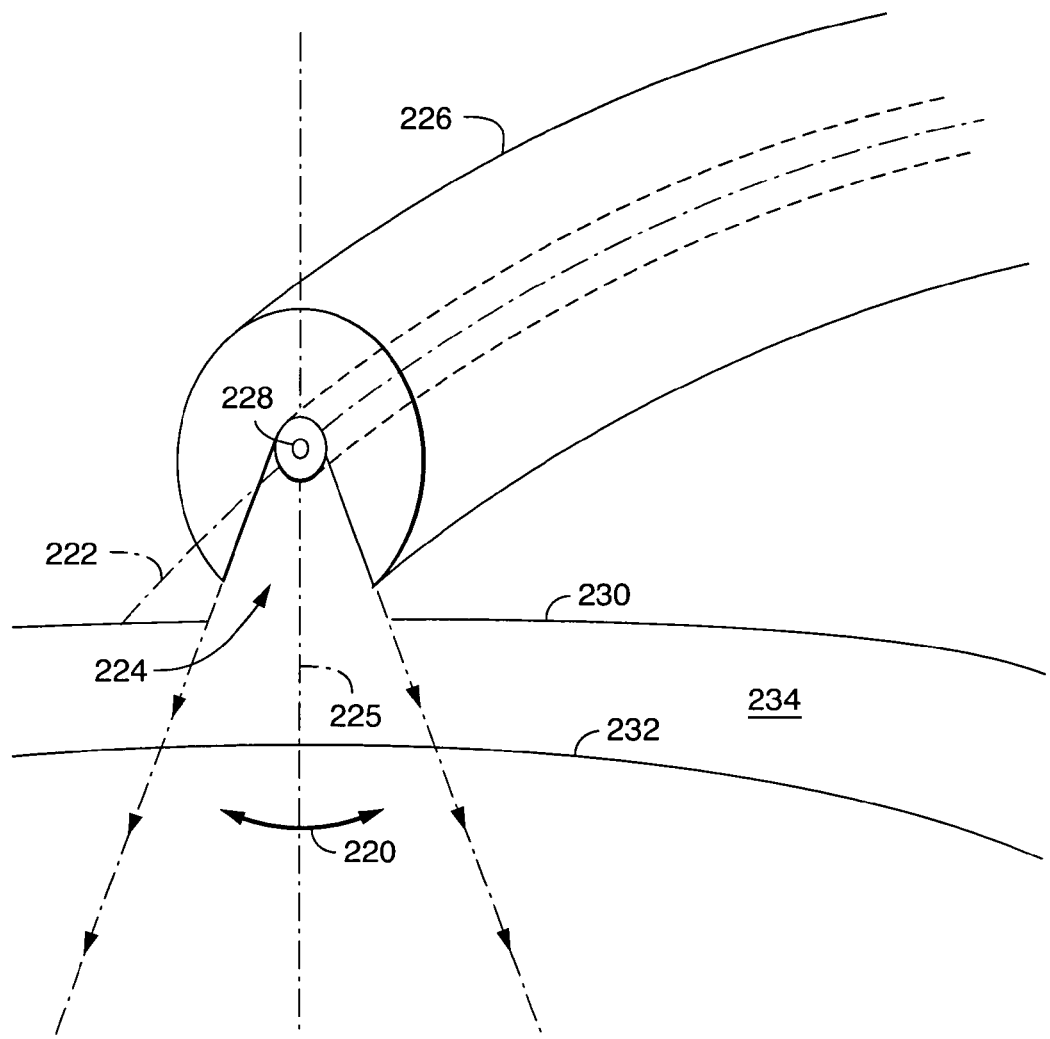
Figure 13:
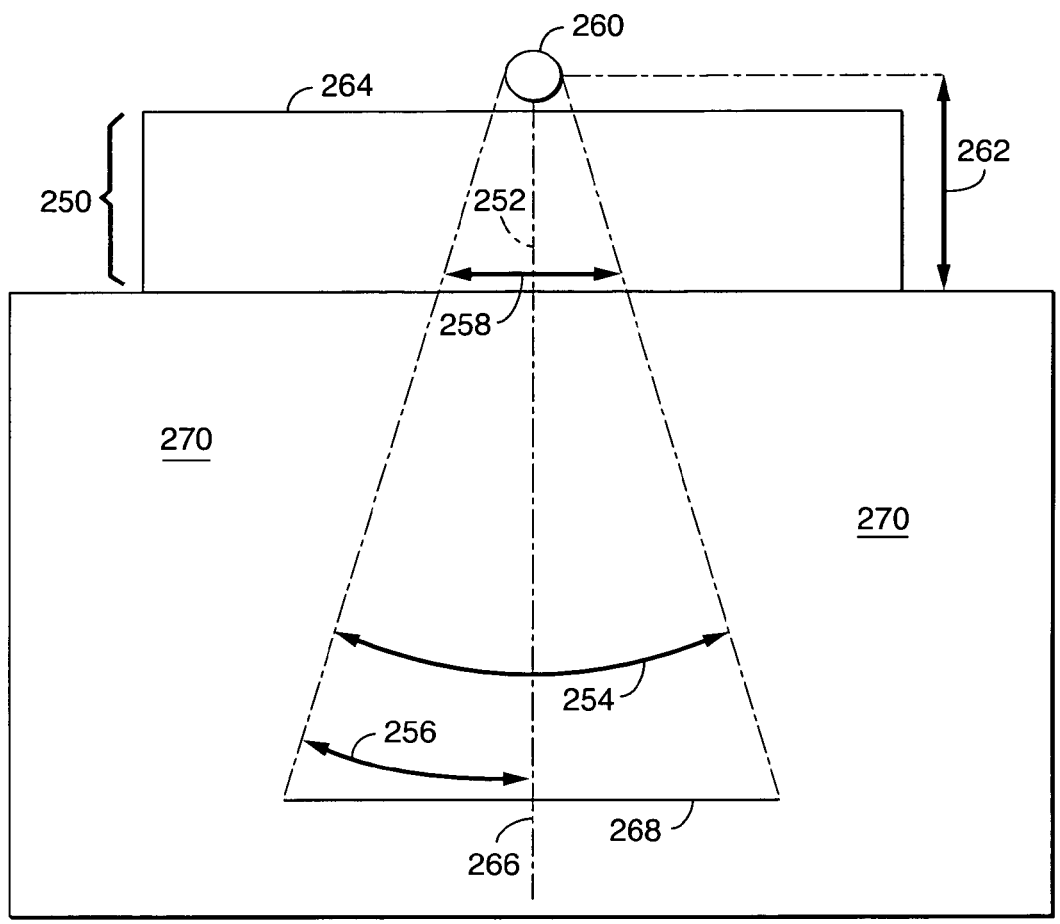
Figure 14:
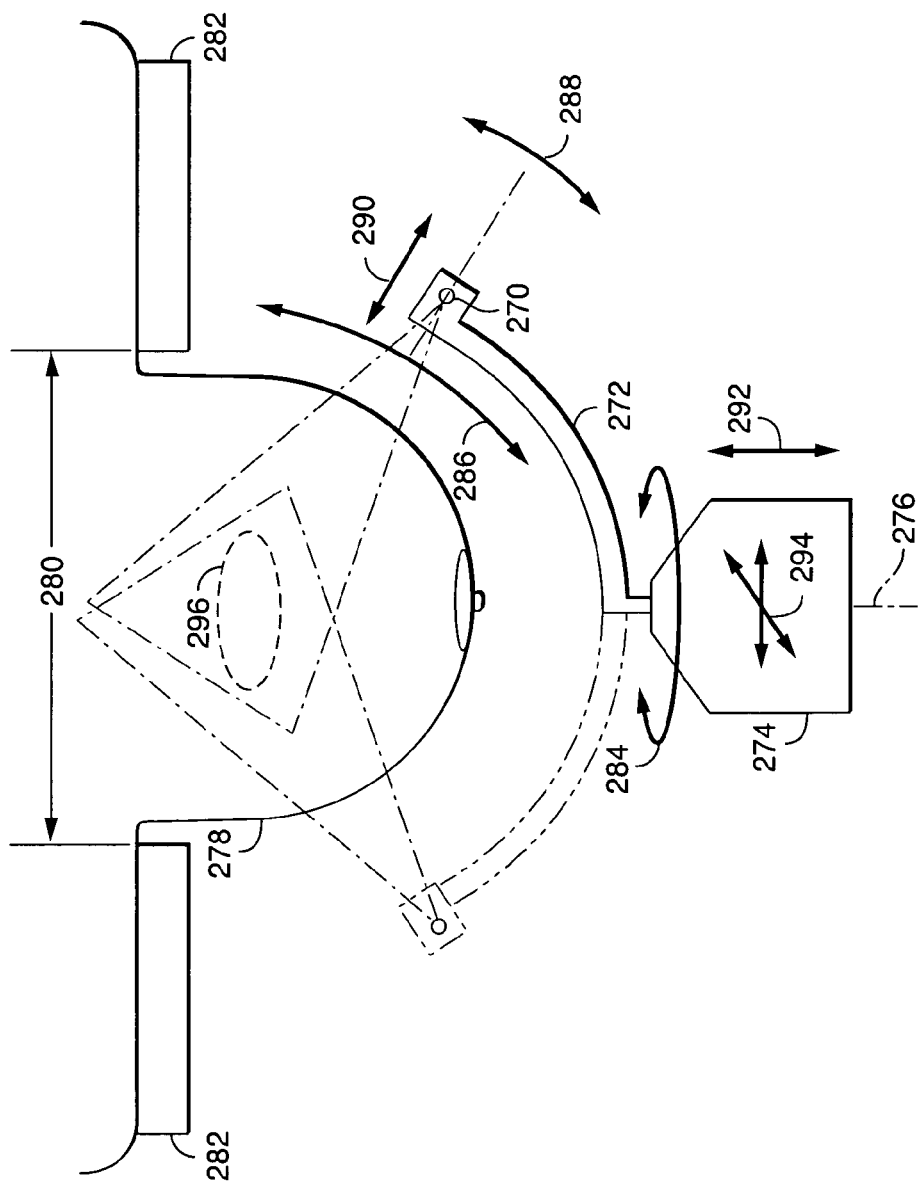
Figure 15:
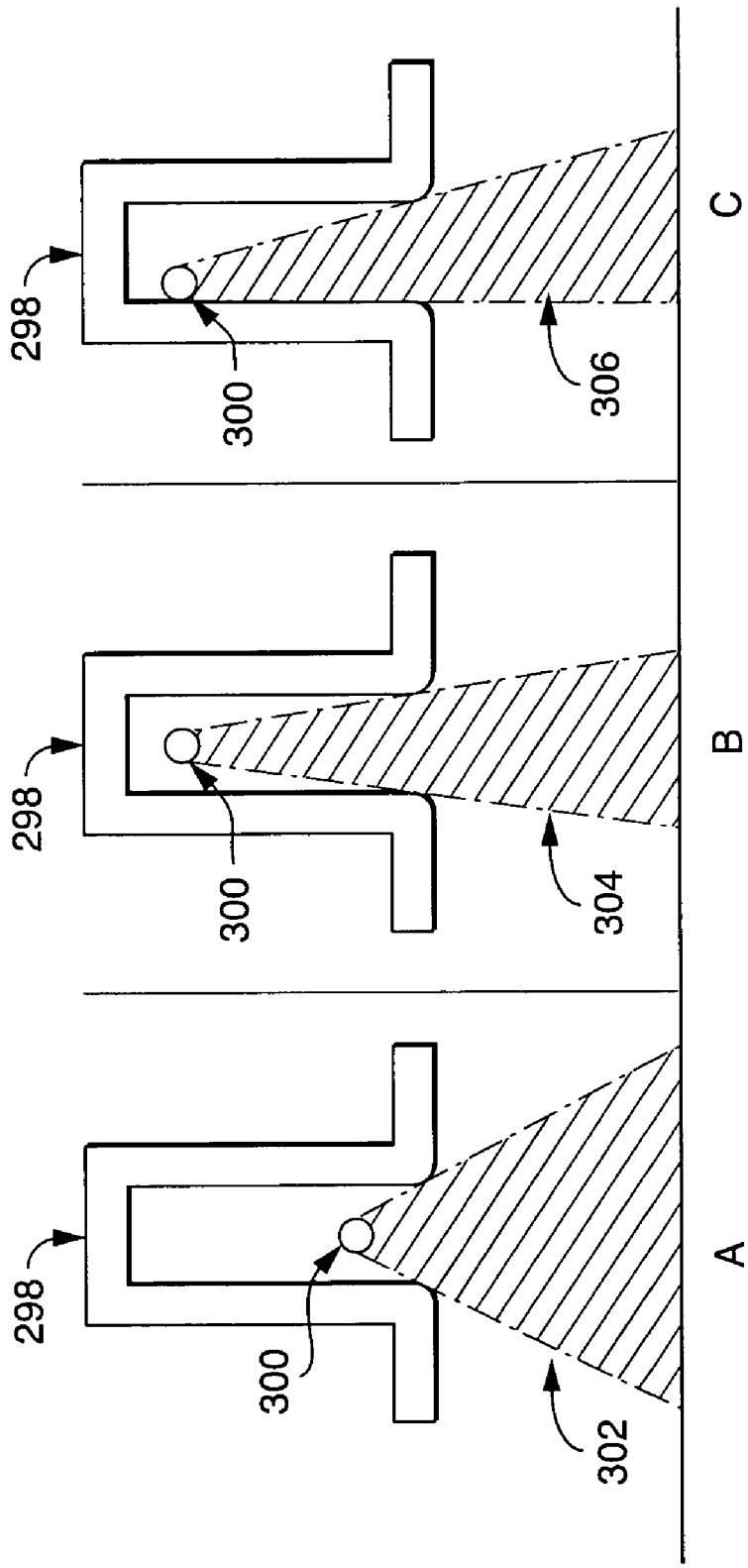

FIGS. 9A and B represents a typical program flowchart indicating primary calculations to be performed, major inputs (both static and dynamic) and major decision making paths in a typical treatment sequence;

FIG. 10 is an illustration of multiple field shaping cells used to control the relative dose of radiation to the skin vs. dose to the center of the target volume;

FIGS. 11A and B illustrate two examples of the orientation of the field shaping cells used to control the exposure of tissues to radiation;

FIG. 12 is a perspective schematic view of an example of a continuous field shaping cell;

FIG. 13 is a perspective schematic view of an example of a single conical field shaping structure/cell;

FIG. 14 is a perspective schematic illustration of an example of an applicator using a robotic arm; and FIGS. 15A-C are cross-sectional views showing the effects of positioning a source within a field shaping structure on the divergent shape of the radiation pattern emitted from the field shaping structure.

DETAILED DESCRIPTION OF THE DRAWINGS

The devices and methods described in this disclosure are particularly suitable for treatment of a large, designated or targeted volume (on the order of a few to tens of cubic cm, or greater) within a protruding organ, such as a breast, testicle, or penis. In one embodiment the devices and methods require one or more divergent beams or patterns of therapeutic radiation from one or more radiation sources placed within an applicator supported relative to the surface of a protruding organ. It should be understood that as used herein, reference to a "source" or "sources", in each instance, can mean either a single source adapted to be configured and/or moved so as to radiate in more than one direction toward the targeted volume, or a distribution of two or more sources similarly adapted to be configured so as to radiate in more than one direction, so as to concentrate more of the total exposable radiation in the targeted volume, than in the surrounding tissue. The applicator is affixed relative to the organ for each exposure by the source or sources, and provides a stable platform for receiving the radiation source and delivering the dose to the designated volume independent of target movement (e.g., due to breathing cycle). The definition of a designated volume as well as the relative positioning of the source or sources in the applicator can be correctly identified by imaging guidance techniques for proper alignment and monitoring of the delivered dose. In one application, the source(s) must be positioned within a narrow range of distances from the skin. Placing the source(s) too close to the skin (e.g., less than about 3 mm) can cause excessive skin exposure; while placement farther than a few cm (e.g., 5 cm) away from the skin can result in the intensity of the dose falling off and the brachytherapy becoming inefficient, and therefore insufficient and ineffective. By proper source placement(s) relative to the targeted volume during treatment, multiple divergent beams can be directed to overlap or intersect solely in the targeted volume. This, in turn, results in the exposure fields being superpositioned within and thus provide the therapeutic dose to the targeted volume, while the portion of the volume that is not exposed to the intersection of the divergent beams receives a sub-therapeutic dose.

The disclosure also describes the design and utilization of a non-invasive brachytherapy technique where a distributed radiation source pattern is created by using one or more sources. The source or sources can include, but not limited to, one or more isotopes, one or more discrete sources, and/or one or more generators of ionizing radiation. During treatment, the portions of a single source or the multiple sources that provide the therapeutic dose are preferably distributed in or sequentially moved to predetermined fixed positions at a close predetermined distance to the skin around a protruding organ, and moved and/or arranged so that a prescribed therapeutic dose is delivered to the targeted tumor or tumor bed within the organ. Imaging guidance is preferably, but not necessarily, used to locate and define the designated target volume within the organ to which the radiation will be delivered. The prescribed dose delivered to the designated volume can be determined, for example, by calculating the total cumulative or sum of the superpositioned lower doses respectively delivered to the designated volume from the distributed positions arranged around the targeted tissue. Alternatively, computer simulation techniques can be employed to determine the superpositioned or superimposed (cumulative) dose delivered to the desired volume taking into account the shape, size, volume of the designated targeted tissue and its location and distance from the skin.

A protruding deformable organ, such as the breast, offers a unique geometry for radiation therapy from the periphery. It allows a non-invasive applicator to be designed (and accordingly facilitate a procedure for treatment) such that the applicator may, in the case of a breast, for example, modify the shape of the breast, and allow a source or sources of radiation to surround, or be positioned at two or more locations at the periphery of the organ, so as to allow for a pattern of overlapping, intersecting beams of diverging radiation from two or more directions/angles to increase the cumulative dose to the inner targeted tissue, or designated volume, within the organ, and fix the distance of the source(s) at each of the locations from which each beam of diverging radiation is directed. This overlap within the designated volume allows the source, or each of the plurality of sources, to deliver lower average doses to the intervening tissue from each of a plurality of positions, while delivering a higher dose to the targeted tissue than otherwise provided when only a single source of radiation is used. Thus, the approach disclosed herein, which in the case of the treatment of breast cancer we term the Peripheral Brachytherapy of the Breast (PBB) concept, has the benefit of limiting the dose to untargeted, otherwise healthy, tissue facing each radiation source location. This is not possible with teletherapy sources or beams of radiation available from conventional radiotherapy. The limited penetration from the radiation source(s) advocated in this disclosure along with the geometry of and the relative proximity of the applicator combine to limit the doses to the underlying, adjacent, otherwise healthy tissues surrounding the targeted tissue, while delivering a therapeutic dose to the targeted volume within that organ. The higher dose can be created by various means, all of which involve effectively surrounding (or at least positioning at select locations around the periphery of) the deformable protruding organ. The source(s) are preferably positioned in three-dimensional space so that the source at each position is a predetermined, relatively fixed position from the targeted volume, and the fields generated at each source location constructively add within the targeted volume, thus, collectively producing the therapeutic dose levels at that location. A source may be placed at each of several of the locations at the same time and/or a source may be moved to each of several positions over time during treatment. This disclosure contemplates that the source or sources of radiation provide point sources (substantially one dimensional), line (not necessarily straight) sources (two dimensional) and/or broad planar (not necessarily flat, but extending in three dimensions) sources so as to create the overlapping radiation pattern that provides accumulated dose at the targeted volume. The radiation source(s) can include, but are not limited to, radioisotopes or generators of ionizing radiation (x-ray or electron sources).

The embodiments of the method and system disclosed herein are particularly useful for brachytherapy of a breast carcinoma following a lumpectomy where the cancerous breast tissue has been surgically excised, although it should be appreciated that other applications can be provided without undue experimentation. Following a lumpectomy, to prevent local recurrence, there is a need to expose the tumor bed to radiation to "sterilize" the field and destroy pre-cancerous micro-inclusions that may still exist near the original site that would otherwise result in a local failure. Typical brachytherapy doses delivered to the breast following lumpectomy have ranged from about 10 Gy to about 50 Gy. The specific dose depends on the dose rate, fractionation schedule and the duration of therapy, nature of the original growth, mono versus boost therapy, as well as host of other factors which will be evident to one skilled in the art. A typical target for partial breast brachytherapy is a volume extending from about 2 cm beyond the lumpectomy (excision cavity) margin. Using the presently disclosed Peripheral Brachytherapy of the Breast (PBB) concept, one can deliver a sub-therapeutic dose to substantially the entire breast and a therapeutic dose to the target volume within the breast. The prescribed therapeutic dose to the typical designated volume of the breast is usually in the range from about 15 Gy to about 40 Gy. The therapeutic dose depends, among other factors, on the duration of radiotherapy, where the shorter the duration of radiotherapy the lower the dose. The primary alternative (the current "standard of care") is total breast irradiation by an external beam that is typically delivered in 5 to 7 weeks with daily doses of about 1.8 Gy, for a total dose of about 45 Gy.

Generally accepted practice is that radiation therapy for breast cancer is expected to be completed within 60 days, which is the maximum expected duration for the PBB approach, although the period could vary beyond 60 days. More typically, using the PBB approach, the treatment is expected to be delivered from about 2 days to about 10 days.

In accordance with the disclosed system and technique, peripheral breast brachytherapy can be performed with the patient in any one of many different positions. The patient may be treated, for example, while lying in a supine or prone position. In the prone position, special tables may be used. The tables can each include, for example, a properly positioned hole or aperture for receiving the breast, so the breast can hang freely by the force of gravity. Alternatively, the patient may be treated while standing up or sitting down. The organ, especially when treating the breast, may be conformed, or fitted within a confined space so as to ensure a fixed relationship between the position of the target volume and the position(s) of the source(s) during treatment. Varying the patient's orientation or movement of the target volume during treatment, relative to the source(s) relative to the treatment and imaging system, or movement of the target volume relative to the source(s), will impact the ability to target and treat certain predetermined volumes within the breast, as well as increase stray doses to other organs and tissue. Thus, the positioning and orientation of the patient, and whether the breast is confined during treatment may actually depend in part on the location of the targeted volume.

For treatment of a conformable protruding organ like the breast, the source(s) of radiation can be placed in a special applicator. The applicator, when supported relative to a conformable organ, will preferably fix the shape of the organ relative to the source(s) during treatment, and provide a stable platform that delivers a constant radiation field independent of the body motion generally, or organ motion specifically, due, for example, to the breathing cycle. The applicators can be designed to either conform to the shape of, or surround, the protruding organ thus allowing for the secure placement of the source(s) at the periphery of the organ in close proximity to its surface. Alternately, the applicators may include a cavity for receiving the organ, and may be made of a rigid material and rigid geometry such that the protruding organ is forced to take the shape of and thus conform to the shape of the cavity within the rigid applicator. The applicators further preferably include cells, pockets, recesses, and/or lumens for the insertion and movement and/or attachment of each source of radiation at the prescribed positions of treatment.

Compression plates are commonly used in mammography procedures. The compressed breast presents a flat uniform tissue mass and is easier to radiographically image for identification of calcification or cancerous lesions. Similarly, compressed breast tissue presents a more uniform target for radiotherapy. The present disclosure includes a method of compressing the breast between two plates to present a uniform mass for imaging and radiotherapy. In particular the orientation of the compression can be altered to image and irradiate tissue from different angles. The compression of the breast tissue, due to its deformable nature, causes the organ to spread laterally and thus can reduce the amount of normal tissue between the treatment plates and the designated volume. This can cause the dose to the normal tissue of the breast to be substantially reduced. Two orthogonal compression plate orientations or a plurality of compression plate orientation angles can be used to perform imaging and radiotherapy. In the process of using different compression plate orientations for radiotherapy, the dose to the designated volume is accumulated while the skin dose is divided between different points of entry, thus controlling the skin toxicity. A preferred angle for both radiographic imaging and radiotherapy is the direction perpendicular to the compression plate. Imaging at each compression plate orientation allows for targeting the radiation field to match the designated site.

An embodiment of the present disclosure is to irradiate the margins of a lumpectomy cavity. Two compressions of the breast from two orthogonal planes allow radiotherapy from 2 orthogonal planes and enables the accumulation of dose to the designated target without exceeding the toxicity limit of the skin. The apparatus that can provide compression, image registration and radiotherapy is part of the disclosure.

Thus the applicator may take the form of a set of applicator plates, either of which, or both may include the structure for housing a source or sources of radiation near the surface of the protruding organ. These plates are preferably disposed parallel to one another and may be used to compress the protruding organ. The plates may also be curved such that they are designed to conform to the general shape of the organ so as to reduce any discomfort for the patient, yet still be able to press against the organ so as to compress the organ into a desired shape, and fix the targeted volume relative to the source(s) positions during treatment. Further, the applicators can include an elastic, flexible or pliable structure for conforming to the organ and keeping the applicator in intimate contact with the organ to deliver a constant and consistent dose from prescribed directions and distances to the targeted volume. An additional function of the applicator may include lifting and separating the protruding organ from the neighboring parts of the body so as to minimize stray radiation doses into those neighboring parts. The applicator is preferably placed in contact with, or communication to, the surface (periphery) of the protruding organ which is being treated so as to fix the source(s) relative to the target volume at each treatment position. As a result, unlike conventional teletherapy approaches, the delivery of radiation to the organ is unaffected by the motion of the patient, such as motion associated with breathing.

To minimize stray radiation doses (doses to any other untargeted tissue, organ or person), the applicator may additionally include an attenuating or shielding outer layer. Typical attenuating and shielding layers are made of high atomic number, dense materials, but the specific selection of the attenuating material will depend upon the particular organ, radiation source and treatment plan. The applicator may include an inner layer designed for direct contact with the skin which can control the distance of the radiation source from the skin. The thickness of such an inner layer should reduce the intensity of the skin dose for that portion of the organ facing the radiation source. The inner layer may also include high water content, and may include a water filled sponge and/or gel media or water-equivalent materials.

Additional attenuating materials, apertures and structures may be incorporated into the applicator such that they provide structure for controlling and thus determining the direction(s) of the exposure field. These field-shaping structures may include, for example, masks, bands and/or sheaths of attenuating material, or grooves within an attenuating material into which the sources are placed. The structures can also be made of field shaping cells for receiving radiation source material. The field shaping cells may be designed in such a way as to limit the side exposure while providing the full exposure of, and thus define the shape of the beam of radiation that is used to expose the tissues directly in front of the cell or set of cells. The design of these cells (including the height, aspect ratio, attenuator material, attenuator thickness) thus can be used to selectively shape the radiation exposure field. Where HDR applicators are used, the field-shaping cells may be included and preferably placed along the path of the HDR lumen(s) so as to coincide with the dwell positions of the sources.

Patient positioning and image guidance are important to precisely target radiation to a designated volume within a protruding organ. In the case of a breast, various imaging methods including, for example, x-rays (such as mammography or CT scanning), ultrasound, fluoroscopy, MRI, and portal imaging, may be used for imaging the tumor or tumor bed and determining the radiation targets. Similarly, different radiographic or ultrasonic fiducials, such as implantable markers, skin tattoos and contrast media are commonly used to mark the tumor bed (the margins of a lumpectomy cavity). Image guidance is usually of vital importance for radiotherapy of the breast as the breathing cycle presents a moving target. The present disclosure describes an embodiment designed so as to (a) facilitate the positioning of radiation source(s) in an applicator that is/are mounted to the breast and (b) deliver constant radiation to the designated volume within the breast independent of the breast tissue movement during the breathing cycle.

The applicators may include one or more markers to facilitate alignment of the applicator with either the protruding organ or the imaging system. The applicator markers are preferably designed so as to be visible by any one or several common imaging technologies (depending on the one used in a specific application). Further, the markers may be tracked by dose planning software to act as an aid to the precise targeting of the radiation field.

Figure 1:
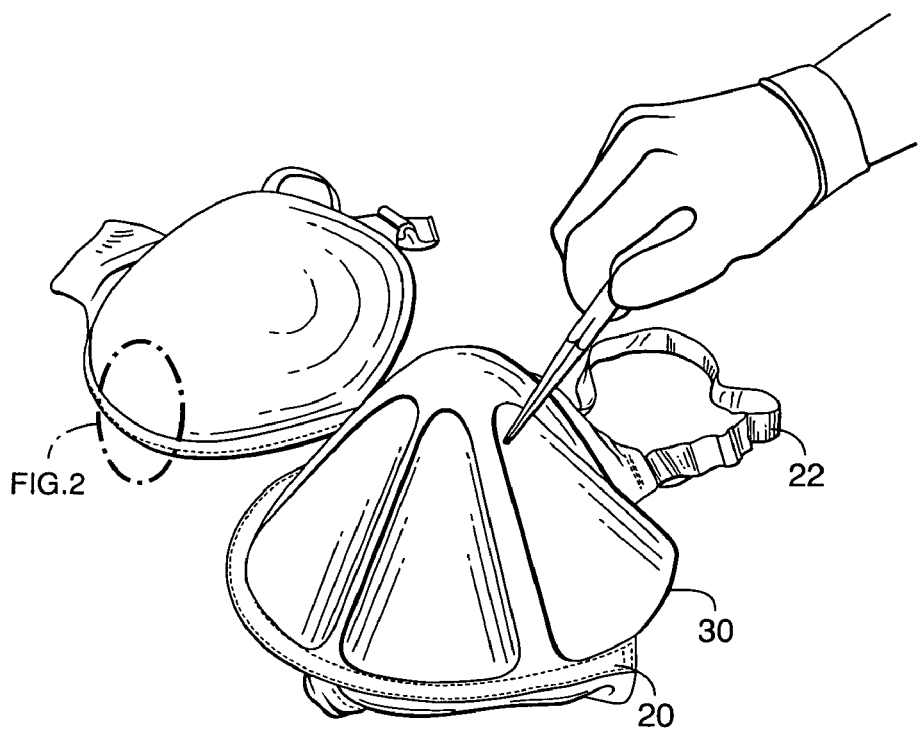
FIG. 1 is a perspective view of one embodiment of an applicator used for brachytherapy treatment of the breast in accordance with the principles described herein.
Figure 2:
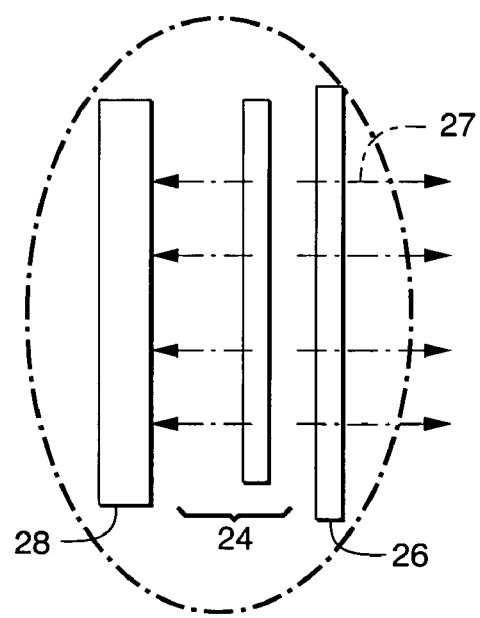
FIG. 2 is a cross section taken through the cup of the applicator shown in FIG. 1 and supporting the breast under treatment.

In one embodiment the applicator bra may include channels, lumens or enclosures for receiving larger source(s). For example, as shown in FIGS. 1 and 2 a bra 20 including support straps 22, the bra 20 includes one or more compartments 24 formed between an inner layer 26 and outer layer 28, and constructed to receive one or more radiation sources 30. The sources can be planar, line or point (or similar structures) sources, as previously mentioned. The configuration of each compartment 24 may vary according to the size of the breast and the size, shape and distance below the skin of the target tissue. In this embodiment the source can be incorporated into a plate, foil, fabric, sheet, wire or point (or other structure) source (a foil being shown in FIG. 2), suitably treated so as to provide the necessary radiation pattern. The outer layer 28 should be constructed to attenuate X-rays, while the inner layer, contacting the skin should be transparent to X-rays. Alternatively an X-ray absorbent plate, sheet, foil or similar structure can be included within each compartment between the source and the outer layer 28.

Figure 3:
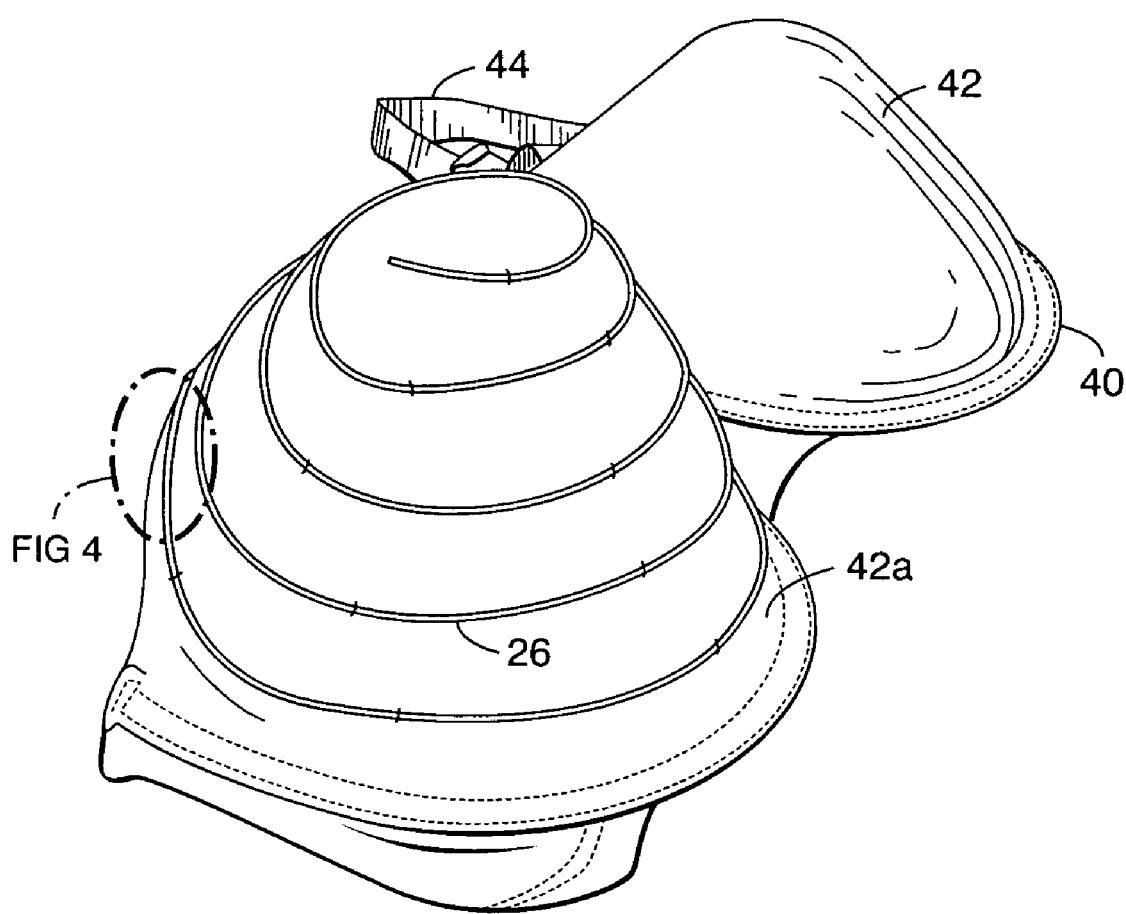
FIG. 3 is a perspective view of another embodiment of an applicator used for brachytherapy treatment of the breast in accordance with the principles described herein.
Figure 4:
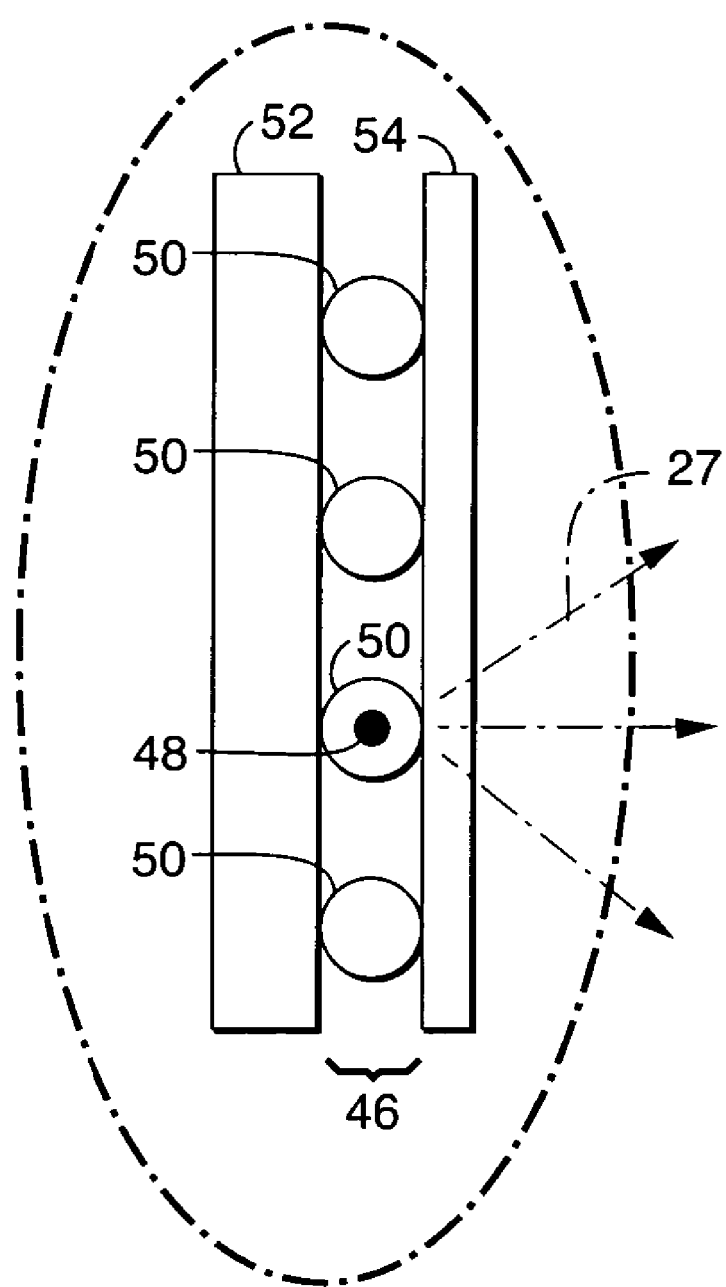
FIG. 4 is a cross section taken through the cup of the applicator shown in FIG. 3 for supporting the breast under treatment.

In the case of the breast, the applicator may be in the form of a brassier, cup or a pouch. In one embodiment of the current disclosure the applicator may be constructed to receive source(s) (such as the bra or brassiere 40 as shown in FIGS. 3 and 4). The bra 40 facilitates treatment of a breast compatible with an HDR afterloader. The bra includes a pair of cups 42 for supporting the breasts and supporting straps 44 so that the bra can be comfortably worn by the patient when in use. The cup 42a used to support the breast under treatment also includes separate internal lumen(s) or compartment(s) 46 for receiving source(s) 48. In the embodiment of the applicator shown, the lumen is adapted to receive a carrier supporting one or more sources. The carrier is preferably, although not necessarily a catheter 50 onto or into which at least one source is attached or inserted. As best seen in FIG. 4, the cup 42a includes at least one outer layer 52 and at least one inner layer 54, defining the lumen(s) or compartment(s) 56 there between. The lumen or compartment shown in FIGS. 3 and 4 has a spiral configuration. It should be understood that the configuration of the lumen(s) or compartment(s) can assume other configurations and geometric shapes to accommodate the source(s). The patterns of the channels, lumens and enclosures may vary according to the size of the breast and the size, shape and distance below the skin of the target tissue. Typical patterns for the lumens would include, for example, substantially straight or curved channels extending in predetermined directions, such as form the base toward the tip of the cup, spiral(s), multiple concentric circles of increasing diameter or a series of lumens which outline a cone or a truncated cone (i.e., frusta-conical shape) of tissue contained within. Clearly, the specific configuration of the cup and the sources can be designed depending upon the particular application and treatment. In this configuration, the patterns of the lumens as well as the dwell times for the source will be determined according to the size of the breast, the size and shape of the designated tissue within the organ and the position of the target with respect to the surface of the organ. The outer layer 52 is preferably made of a shielding material (for example, a fabric containing lead) to absorb, and therefore reduce or prevent radiation emitting outwardly from the cup, while the inner layer 54 is preferably made of a material, such as a fabric that is substantially transparent to the X-rays so as to allow the X-rays to be propagated through the inner layer into the targeted volume of the treated patient's breast. Alternatively, a shielding (X-ray absorbent) plate, sheet, fabric or material (not shown) made be provided between the outer layer 52 and the compartment or lumen. In this latter instance the outer layer need not include an X-ray absorbent material. A suitable opening or openings are provided for receiving the source(s) of radiation into the lumen or compartment.

HDR after loaders useful for inserting the sources, with the aid of a carrier such for as, for example, a catheter, include those that have been designed for use with interstitial, intracavitary or intra-luminal brachytherapy. The HDR after loader system (not shown) typically includes a) a shielded container to house an intense radioisotope source when not in use, b) a delivery system to advance the sources from the shielded container through one or more compartments, channels or lumens, with the aid of the carrier, e.g., catheters or like structures, in place with respect to the patient in the desired area of treatment and c) a control system which monitors and controls the dwell position and time of the sources within the treatment carrier to assure that the dose delivered matches the dose prescribed. In the brassier applicator of the type shown in FIG. 3 and 4, using the lumens for source placement, the dose to the underlying tissues is controlled by adjusting the dwell position and dwell time. Further, in this embodiment, one or more field shaping cells prepositioned in the lumen can be used or positioned in relationship to the source(s) so that they coincide with the dwell positions of the sources. Alternatively, a continuous aperture along the lumen may be employed for controlling the dose to a designated volume to reduce the relative dose to the skin or healthy tissues such as the heart, lungs or contralateral breast.

In the case of the present disclosure, it is further contemplated that there be the option of a control system, preferably including a computer program arranged so as to control the dwell position of the source(s) within the lumen(s) of the applicator.

The control system preferably will require parametric inputs, both static and dynamic, which can include geometrical factors (source size, shape, applicator size and shape and others), dose prescription factors (dose, dose rate, target tissue and others), biological factors (target tissue, margins, sensitive tissue locations and others), source factors (size, shape, activity, activity distribution) and dynamic factors (patient and operator readiness, proper mechanical positioning and operation verification, position telemetry and others) to provide process/procedure control. The control system may also include options for user intervention, overrides, monitoring, and reporting.

A computer program may be used in the treatment planning process. This program will offer the option of (a) defining the dose distribution to the protruding organ, or to a designated targeted volume within the organ, and (b) determining an appropriate distribution of source(s), field shaping cells and/or dwell times along the periphery of the organ. The computer program could also allow the user to define the source(s) and/or field shaping cells and their locations, and calculate the dose distribution within the organ. In any case, the program may accept one or more of the following parametric inputs: the number, type, species, intensity, shape, activity distribution, size, etc. in determining the required placement of, or resulting dose distribution from the sources. Further, the number, type and characteristics of field shaping cells, if used, may be included in the determination. The treatment planning software program may include the option of enabling the alignment of the coordinate systems of the treatment planning software with that of the protruding organ, applicator or imaging system. The use of the markers on/within the applicator along with either reference anatomical landmarks or applied imagable markers on or within either the protruding organ or the applicator may be used by the program to facilitate the overlay of the coordinate systems of the software program and one or more of the following: the organ, the applicator and the imaging system. Alternately, the position of the target tissue may be determined by an imaging modality that is directly incorporated into, or in communication with, the treatment system that provides input data to the computer program. Multidimensional images of the organ and associated structures may be imported by the software program to facilitate this alignment. Options to calculate the placement of sources based on a combination of dose to the designated volume and a dose limitation to neighboring organs or tissues may be included. The software program may also include the option of real-time feedback on dose delivered to the targeted tissue where the future source positions and dwell times are recalculated as often as desired based on the historical dose delivery feedback.

The radioisotope(s) may be transmuted within the source carrier (e.g. by direct nuclear activation) or may be dispersed into, or applied to, the surface of carriers by any number of chemical or physical methods, simple adhesion or encapsulation. Examples of some of the more common methods include the processes of plating, painting, sputtering, reaction bonding, encasement of radioisotope dispersion within a polymer and the like. Other methods may also be employed.

The radionuclide(s) of the source(s) could be chosen from the list of commonly recognized and/or available radionuclides. The ideal isotope has the right combination of half-life, gamma ray energies and ease of production and purification. The half-life has an impact on the shelf life of the product. The x-ray or gamma ray (photon) energies control the depth of the field for dose delivery and may be optimized such that it matches the volume and location of the tumor bed. Higher energy photons are better for more deeply seated targets. Finally, the radionuclide must be chosen among available or easily producible species. The primary current options for radioisotopes capable of meeting these requirements include, but are not limited to Co-56, Co-57, Co-58, Co-60, Zn-65, Pd-103, Cd-109, I-125, Cs-131, Cs-137, Sm-145, Gd-153, Yb-169, W-187, Ir-192, and Au-198, though other sources can, and in the future may, meet these criteria. To treat organs of the general size as defined in this application, the energy of the primary photon emissions should be limited to the range of between about 20 KeV and about 1500 keV. For the breast, the energy of the primary emissions of preferred sources are preferably generally between about 50 keV and about 1300 keV.

The radioactive source(s) contemplated in this disclosure can be generators of ionizing radiation, delivering a diverging exposure field, such as x-ray sources or electron sources that can be placed peripheral to the protruding organ. An example of the radiation source is an orthovoltage x-ray source. The dwell position of the generators and the intensity of the emissions can be controlled to deliver the desired therapeutic dose to a target volume within a protruding organ as a result of the superposition of the fields from the individual source dwell positions. Field shaping structures, as described earlier, can be added to the generators to shape the exposure field.

The current brachytherapy applicator is different from previous applicators as it is suitable for treatment of a large designated volume within a protruding organ. It requires at least one divergent beam from at least one radiation source placed within an applicator mounted on the surface of a protruding organ. The applicator is affixed to the organ and provides a stable platform for receiving the radiation source (s) and delivering the dose to the designated volume independent of the target movement (e.g., due to the breathing cycle). The designated volume as well as the applicator are initially identified by imaging guidance for proper alignment and monitoring of the dose. The source must be within a narrow range of distance from the skin. Placing the source too close to the skin (less than about 3 mm) results in excessive skin exposure; while placing the source farther than about a few cm (e.g., 5 cm) away from the skin results in the intensity falling off, the range of allowable frontal exposure angles being restricted and the brachytherapy becomes inefficient. The overlap of the divergent beams where the exposure fields are superpositioned provides the therapeutic dose while the portion of volume that is not exposed to the intersection of the divergent beams receives a sub-therapeutic dose.

It should be appreciated that the distributive effect can be achieved by a single extended or multiple segmented sources and single or multiple field shaping cells. In the case of a single extended source, the single source is configured to extend over an area so as to radiate from different directions or angles toward the targeted tissue or designated volume such that the radiation field from one portion of the source is superpositioned upon the field generated from other portions of the same source so as to constructively overlap and provide the desired dose to the targeted tissue or designated volume.

By creating a proper radiation pattern, the method and product allow for a higher concentration of radiation to be delivered non-invasively to the targeted tissue or designated volume than a source which delivers radiation from a single point source or from a source where radiation is emitted at one position (a planar or a line source), while reducing the exposure of surrounding tissue to incidental radiation.

Figure 5:
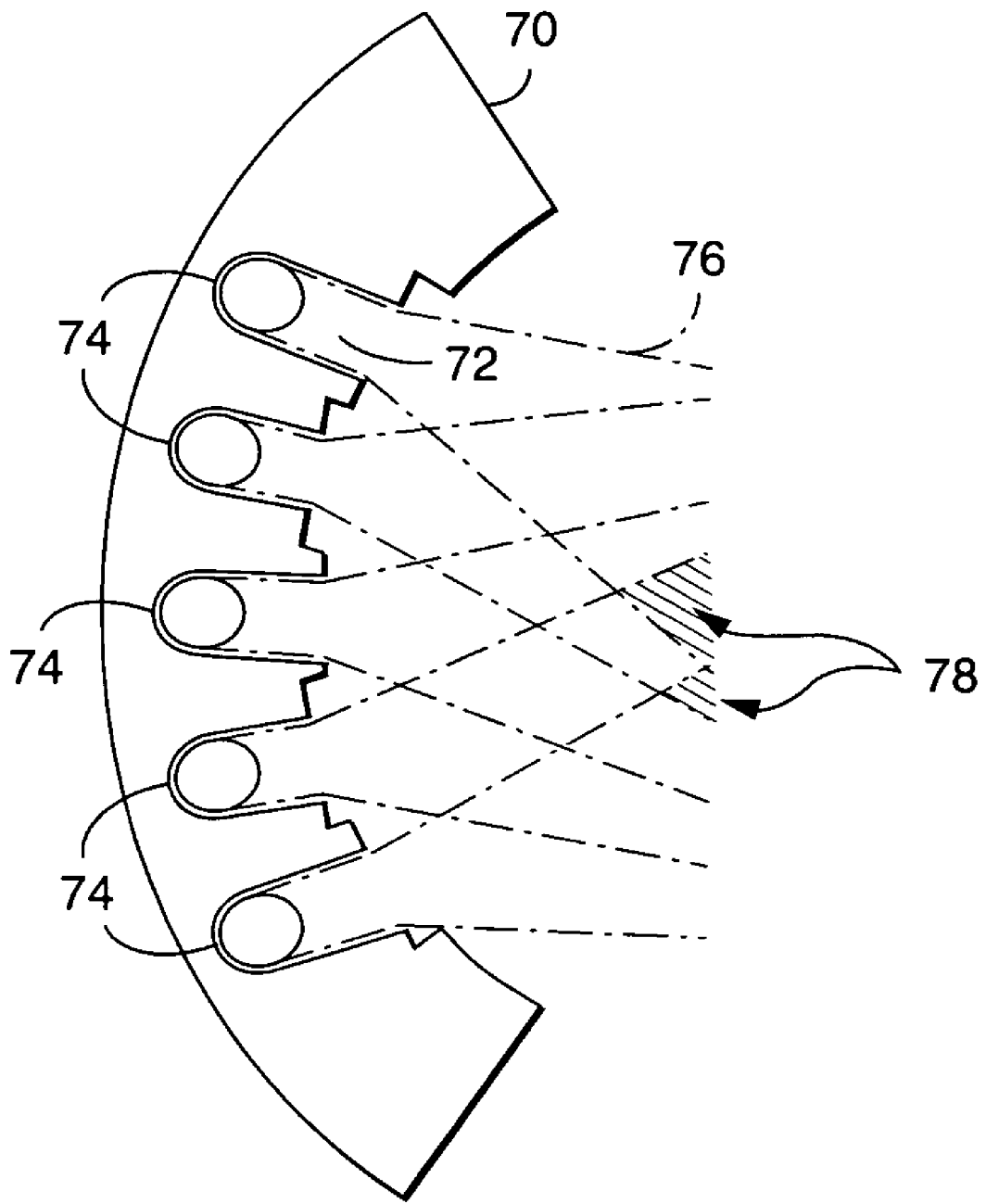
FIG. 5 is a cross section of a portion of an applicator including attenuators having embedded sources to facilitate directional delivery of radiation from each of the sources.

FIG. 5 shows an example of embedded field shaping structure (with one or more apertures) within an applicator to facilitate directional delivery of radiation, and achieve the desired overlap, or superposition, of radiation patterns in predetermined volume of interest. As seen in the drawing, the illustrated embodiment includes attenuating material that is preferably a part of the applicator. The attenuating material 70 is preferably provided with a plurality of channels 72 within the attenuator. The source(s) 74 are preferably embedded in the respective channels so as to form directional diverging beam patterns 76. The source(s) 74 are positioned relative to the target area 78 so that the patterns 76 overlap each other in the target area 78 so that so that a higher dose of radiation is delivered to the target area 78 than the surrounding areas.

Figure 6A:
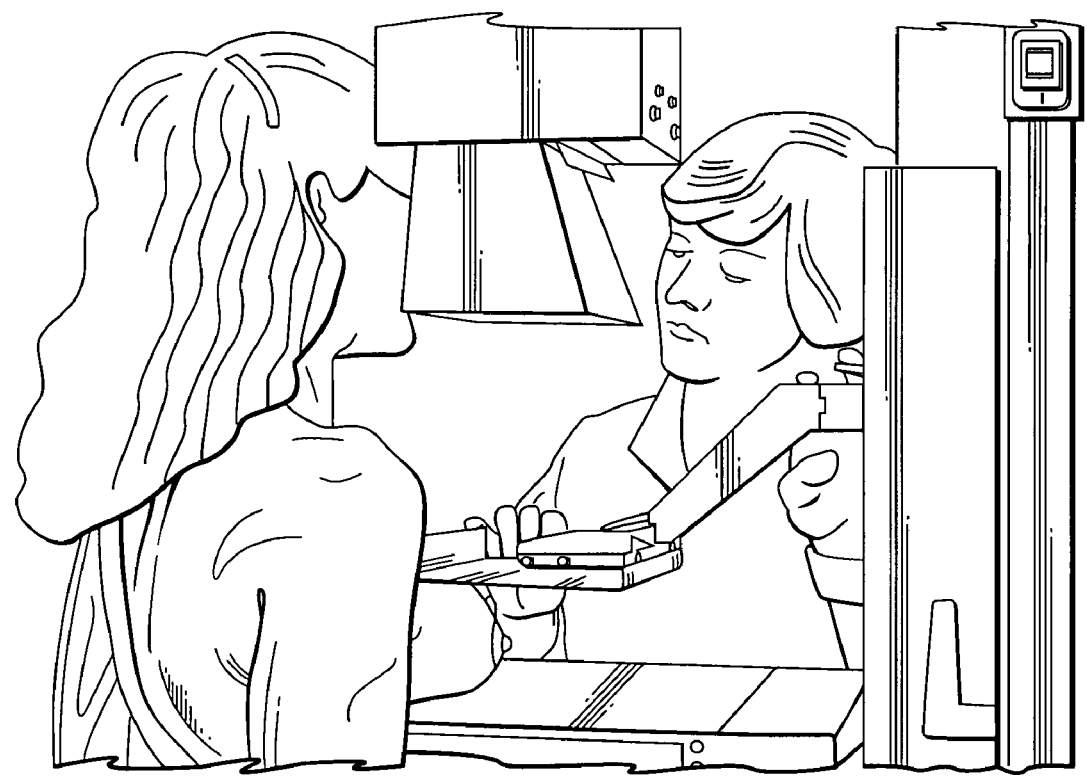
FIGS. 6A-6D illustrate an embodiment of a sequence of steps for providing brachytherapy to the breast using a parallel plate applicator and a dedicated imaging mammography system.
Figure 6B:
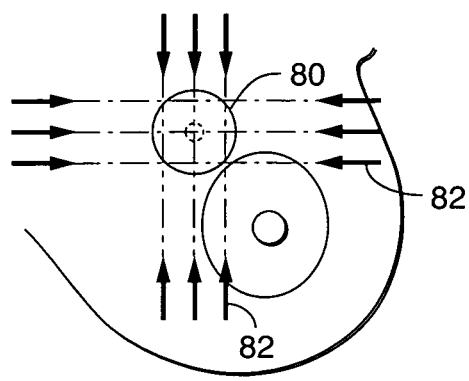
Figure 6C:
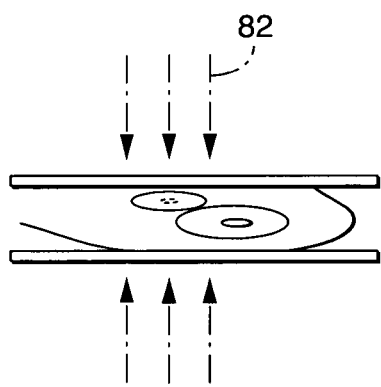
Figure 6D:
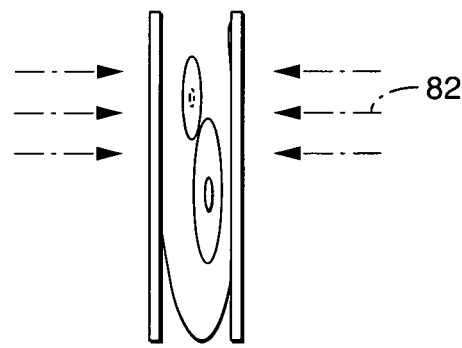

FIGS. 6A-6D show the elements of a non-invasive peripheral breast treatment using a parallel plate applicator approach. FIG. 6A shows the initial imaging of the breast using a standard mammographic technique. In FIG. 6B, the location, size and shape of the lesion 80 are converted to a treatment plan involving treatment from two substantially orthogonal directions 82 and 84, any where from 60 to 120 degrees from the original orientation. Each plate can define a plurality of individual source locations (as illustrated for example in FIG. 8B). In FIG. 6C the first treatment is delivered by a series of HDR source dwell positions within each of the treatment applicators the direction 84. In FIG. 6D, the next treatment fraction is provided at a 90 degree angle with respect to the first treatment fraction in the direction 82. Additional treatment fractions would be performed until the entire therapeutic dose to the target tissue is achieved. In one embodiment, the follow steps are followed in order to apply radiotherapy to a breast. The method of application comprises:

A. Compressing the breast between two plates so as to define the initial treatment plane;

B. Imaging the breast in the initial treatment plane while it is immobilized to identify the designated volume of tissue in need of radiotherapy;

C. Delivering radiotherapy divergent radiation to the designated volume while the breast is immobilized from a direction within an angle of 30 degrees from normal to the initial treatment plane;

D. Removing the compression plates and rotating the compression plates to a new orientation which is within 60 to 120 degrees of the initial treatment plane, and re-applying compression to immobilize the said protruding organ at the new orientation;

E. Identifying the designated volume by imaging, or other means, within the protruding organ from the new orientation;

F. Delivering radiotherapy to the designated volume while the protruding organ is immobilized in the new orientation from a direction substantially normal to the compression plates; and G. Repeating steps D to F, as needed until a therapeutic dose is delivered to the designated volume within the protruding organ.

It should be apparent that while the embodiment described in connection with FIGS. 6A-6D employ two orientations of the compression plates, the technique could employ more than two orientations, depending on the application and/or desired treatment.

Figure 7:
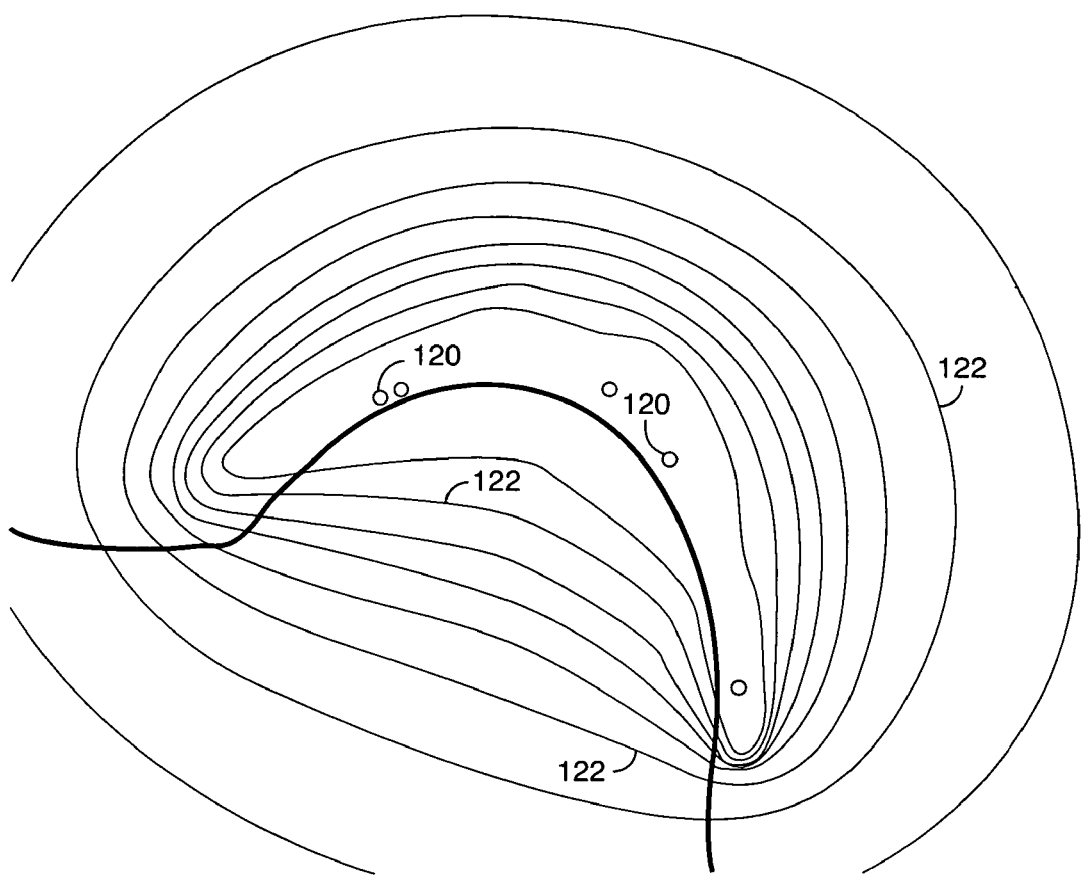
FIG. 7 is a cross-section of an example of a dose map overlaid onto a CT image from a prototype bra-style applicator mounted on a phantom to show the isodose distribution to the breast using a "lampshade" style HDR catheter pattern.

FIG. 7 illustrates an example of a cross-sectional isodose map overlaid onto a CT image from a prototype brassier-style applicator mounted on a phantom 121 to show the isodose distribution generated by an HDR source pattern. That portion of the source dwell positions along the periphery of the breast which fall in this plane are highlighted as points 120. The isodose contours 122 indicate a typical uniformity pattern that can be generated from this source distribution structure.

Figure 8B:
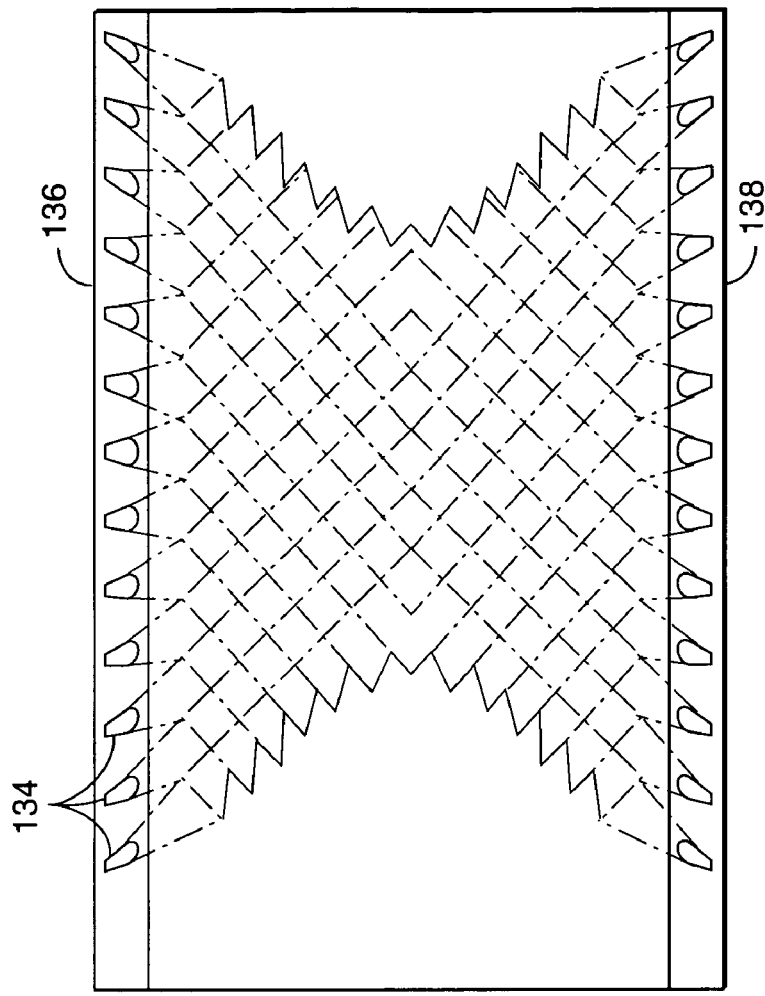
FIGS. 8A-8B illustrates an example of finite element analysis (FEA) of the field distribution from a single field shaping cell of an applicator, and a series of field shaping cells placed within the top and bottom plates of a typical parallel plate applicator, respectively.
Figure 8A:
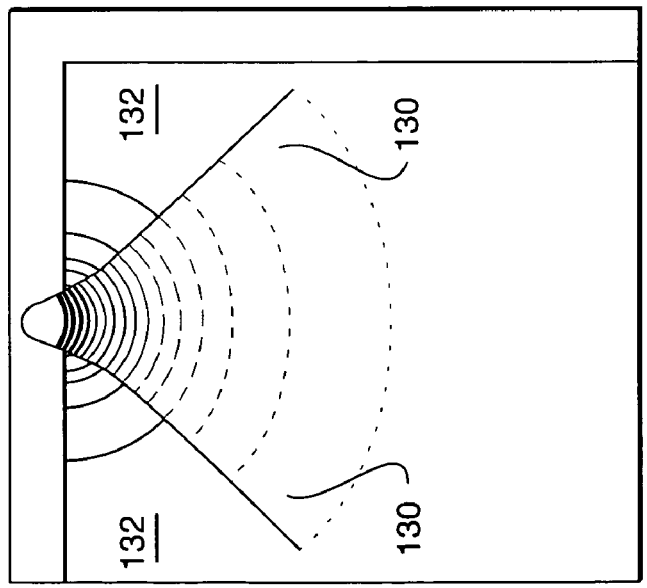

FIGS. 8A and 8B illustrate an example of using finite element analysis (FEA) of the field distribution from a single field shaping cell in FIG. 8A, and a series of field shaping cells placed within the top and bottom plates of a parallel plate applicator in FIG. 8B. In FIG. 8A the 2-dimension field distribution can be determined by finite element analysis for a field shaping cell. In the example shown the cell has an included angle of 90 degrees and a lead attenuator thickness of 9 mm. The angle and thickness can clearly vary depending on the particular circumstances of treatment. This structure creates an unattenuated frontal radiation exposure field 130 and a substantially attenuated side exposure field or zone 132. In FIG. 8B, an example of the impact of this field shaping structure on the 2-dimensional field uniformity between the plates of a parallel plate applicator is shown. In this depiction, thirteen HDR catheter lumens 134 are placed in parallel and spaced 1 cm apart along the top plate 136 and bottom plate 138. The resultant field uniformity is plotted.

FIG. 9 is a typical program flowchart indicating primary calculations, major inputs (both static and dynamic) and major decision-making paths. As shown in FIG. 9, various user or operator inputs include dose prescription factors 150, including dose, duration, dose rate, target volume, and fractionation; geometry factors 152, including shape of the target volume, size of the target volume, form of applicator, source locations within the applicator, source path within the applicator; biological factors 154, including target tissue, margin definition, tissues sensitive to dose (i.e., any "no" treatment areas); and source factors 156, including source shape, source activity distribution, source activity, and source flexibility. The various operator inputs are provided to the program input of the program path, indicated at step 160. Step 160 includes calculating the dose per fraction, dwell times, dwell positions, lumen selection and current dose rates. The results are then presented to the operator as indicated at step 162 for confirmation. The operator can override and revise the calculated dose levels based upon empirical determinations. Once the dose levels are set, the treatment can commence, as indicated at step 164. Dynamic inputs relating to the source, equipment and patient status are then considered (indicated at step 166). These dynamic inputs include patient condition, source position feedback verification, source movement mechanism, operator condition, and program error detection algorithm. These dynamic inputs are provided at step 168 where the source is advanced (placed) in the starting position, and such positioning is confirmed. At step 170, the decision is made whether the treatment at each position is proceeding correctly. This is accomplished by accessing the state of the target tumor(s) in light of the treatment carried out so far. If the starting position of the source cannot be confirmed at step 168, or the treatment is proceeding incorrectly, the step proceeds to step 172 to an error handling module which assesses the problem in light of the dynamic inputs 166. If on the other hand the decision at step 170 is yes, a determination at step 174 is made whether the prescribed dose has been attained. If no, step 170 is repeated. If yes, a determination is made at step 176 as to whether the treatment is in the final position. If yes, at step 178 the source is removed and a determination is made as to as to whether the source is safe. If no, at step 180 treatment is advanced to the next position, and in turn step 170, and subsequent steps following step 170 are repeated for the next position.

Referring again to step 172, once the error handling module determines the error in treatment, a determination is made at step 182 whether the error can be corrected. If yes, a correction or repair plan is determined and the treatment parameters revised at step 184. A determination is made at step 186 as to whether approval for the revised treatment parameters is needed. If not, step 180 and the subsequent steps are repeated. If yes and approval is obtained, at step 188, step 180 and the subsequent steps are repeated. If no, step 178 and the subsequent steps are repeated. Finally, at step 178 the source(s) are removed and the source(s) are verified as safe, reports are produced, as indicated at step 190, and the treatment is ended, as indicated at step 192. It should be appreciated that many of the procedural steps of the flow chart described in connection with FIG. 9 can be implemented by software and stored in suitable memory, such as a CD or ROM of a computer, and operated by the operator on a desktop, laptop, workstation or other similar system.

FIG. 10 is a demonstration of the use of field shaping cells in combination in a HDR procedure. As the example shown, an HDR catheter lumen 200 includes one or more field shaping cells 202, including a HDR source of radiation 204, fixedly attached to or movable within the catheter lumen 200. As shown, the cell 202 and source 204 provide a diverging beam of radiation toward the targeted volume 206. As seen, the field shaping cells can be prepositioned in the prescribed locations for the desired treatment. In this instance a single HDR source 204 can be first advanced so as to move the source 204 through successive cells so that the source 204 is allowed to dwell for a predetermined time at a position within the field shaping cell 202 to deliver a predetermined partial dose from each cell. The process is repeated by advancing the HDR source 204 to each successive position 210 for the prescribed time of exposure. The number of positions and locations is dependent on the particular treatment. Use of field shaping cells limits the side exposure of the dose to the surrounding, superficial tissue (adjacent to the skin) while at the same time allowing accumulation of a larger dose to the predetermined target volume within that organ.

Figure 11B:
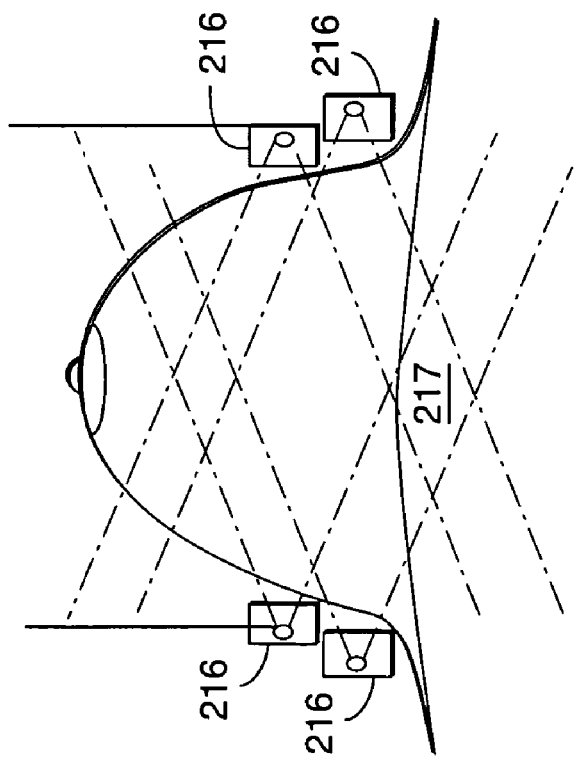

FIG. 11 demonstrates how the orientation of the field shaping cells 216 can be used to control the exposure of tissues to radiation. In FIG. 11A the field shaping cells 216 are oriented perpendicular to the chest wall, treating the breast uniformly, but allowing exposure to positions below the chest wall 217. In FIG. 11B, the field shaping cells 216 are oriented away form the chest wall and thus minimize the dose to positions below the chest wall 217 so as to create a chest wall sparing orientation.

The same results are achieved by using a continuous aperture along the path of the radiation source as show in FIG. 12. Referring to FIG. 12, an embodiment of a continuous field shaping structure is shown as including an unimpeded frontal open angle 220, a longitudinal axis 222 the aperture 224, a radiation attenuator structure 226, such as a catheter containing a radiation absorption material, the lumen 228 for the radiation source, such as either the HDR source or the X-ray generator, the surface 230 of the extended applicator, the surface of the breast 232, the space 234 for the intermediate skin contacting layer between the applicator and the breast surface and the direction of the unimpeded frontal exposure 225.

FIG. 13 shows the elements of an embodiment of a single radiation field shaping structure 250 for creating a diverging beam defined radiation exposure field. Structure 250 includes the radiation absorption material defining an opening 252, preferably but not necessarily conical in shape, defining a frontal open angle 254 (and defining a half angle 256) and aperture 258, the source 260 positioned relative to the aperture 258 by the height or set-back distance 262, and an attenuator 264. The beam of radiation emanating from the source 260 through the aperture 258 is defined by a centerline or beam axis 266, and thus defines the divergent frontal exposure field 268 and the side exposure direction/zone 270. Through variation of open angle 254, half angle 256, aperture 258, distance 262, the divergent exposure field emitted from the field shaping structure 250 can be limited and facilitate the proper overlap of multiple divergent exposure fields with the size, shape and location of the lesion within the protruding organ.

FIG. 14 shows an alternate embodiment of an applicator, utilizing a robotic based applicator. The radiation source 270 is mounted on an arm 272, which in turn is mounted in a support 274 and adapted to rotate about a rotation axis 276. In this arrangement the breast 278 is suitably positioned relative to the application, as for example, allowed to hang by force of gravity through an aperture 280 formed in a patient support 282. Shown are the rotational angle 284, the azimuthal angle 286, source tilt angle 288, source distance variation 290, height variation 292 and lateral displacement 294 of the support 274 relative to the breast 278. The rotational angle 284, azimuthal angle 286, source tilt angle 288, source distance variation 290, height variation 292 and lateral displacement 294 define the six degrees of freedom, and operate in concert to allow the PBB technique to properly align the source(I)( or alternately source and field shaping structure) and source direction at any point along the periphery of, but at a close distance to (within the dimensions previously mentioned) or in direct contact with the breast so as to allow proper tracking or alignment of the divergent exposure field from the radiation source with the designated volume 296 within the breast.

Referring to FIGS. 15A-C, the relationship is demonstrated between the placement of the source or generator of radiation within a field shaping structure and the resultant radiation field. FIG. 15A shows a field shaping structure 298 with a radiation source 300 placed centered and near the aperture generating a broadly divergent radiation field 302. FIG. 15B shows a field shaping structure 298 with the radiation source 300 centered and near the aperture generating a broadly divergent radiation field pattern 302. Finally, FIG. 15C shows a field shaping structure 298 with radiation source 300 placed "off-center" and away from the aperture in the field shaping structure generating a narrowed and asymmetric divergent radiation field 306.

Various additional aspects of the disclosed system and method:

The applicator can custom designed for single patient use. For treatment of the breast, the radiation distribution pattern can be designed so that the dose to the nipple and/or the dose to the excision site is controlled (reduced or increased) as desired. The applicator can include radiation monitor(s) to track/measure the superficial (skin) dose. In those embodiments where the applicator has an inner skin contacting layer, the space between the surface of the breast and the applicator provides a controlled separation distance between the source and the skin. In addition, the inner skin contacting layer of the applicator can be separable from the applicator. In one alternative arrangement, the applicator can include an intermediate layer comprising a high water content or water equivalent material including, but not limited to a water filled sponge, balloon or gel media.

It is envisioned that the primary radioisotope should include a dominant gamma-ray energy somewhere between about 20 and about 1500 keV, and preferably dominant energy somewhere between about 50 and 1300 keV. The radioisotope is preferably selected from a group including; Co-56, Co-57, Co-58, Co-60, Zn-65, Pd-103, Cd-109, I-125, Cs-131, Cs-137, Sm-145, Gd-153, Yb-169, W-187, Ir-192, and Au-198. In one embodiment the radiation source is an orthovoltage x-ray source. The dose can be delivered either continuously or intermittently (by fractions) over a period ranging from between about 10 minutes to about 60 days. It is also envisioned that the radiation dose in each fraction is between about 1 and about 10 Gy and the accumulated dose is in the range of between about 10 to about 100 Gy. The dose to the designated volume during each fraction is preferably between about 3.0 and about 4.0 Gy, and a total dose of between about 30 to about 40 Gy delivered in 8 to 10 sessions over a period of 4-5 days. The non-invasive brachytherapy can be applied intermittently until the prescribed fractionated dose is delivered in each session. The non-invasive brachytherapy described herein can be performed as a boost to other radiotherapy procedures. For example, the non-invasive brachytherapy technique can be combined with hyperthermia, radiation sensitizers or other means of enhancing the effectiveness of the radiation treatment. It should be evident that the dose and treatment can vary. Where the accumulated therapeutic radiation dose delivered is in the range of between about 15 to about 45 Gy, it is preferred that the average subtherapeutic dose delivered to surrounding tissue is at least 20% lower than the therapeutic dose. As previously stated, the source can be applied while the patient is in a prone position, or in a supine position. Alternatively, the source can be applied while the patient is sitting or standing the applicator contains field shaping structures to allow substantially unimpeded divergent frontal exposure to the breast tissue while limiting the side exposure of the superficial breast tissue to decrease the skin dose.

The applicator preferably includes field shaping structure used to create a divergent exposure field. The field shaping structure, made of a radiation absorptive material, such as lead, preferably comprises an aperture with an opening angle extending at least about 20 degrees (half-angle from normal incidence of 10 degrees) but not more than about 150 degrees (half angle from normal incidence of 75 degrees) reducing the side radiation exposure (on the average) by at least 30%. In the case of treatment of the breast, the radioactive source(s) is (are) placed within side exposure limiting structures of the applicator, such as suitably shaped apertures so that the axis of the divergent frontal exposure field is oriented away from the chest wall as to reduce the stray dose to the heart and lungs. In such an application, the open angle of the unimpeded frontal exposure is less than about 150 degrees in at least one plane. In the embodiment where a HDR source is used with the applicator for treatment of the breast, an extended axial aperture structure is used around the HDR source axial path to allow the free passage of the divergent radiation in the frontal direction while limiting side exposure thus reducing the relative dose to the skin as compared to the designated breast tissue dose. The depth of an extended axial aperture channel such as the shown in FIG. 12, can allow the passage of a HDR source and allow the distance of the HDR source from the aperture channel to be varied so that the distance will determine the divergence of the exposure field. Field shaping structures include apertures, masks, shutters, field shaping cells, bands, grooves, or attenuating sheaths and spacers of fixed or variable geometries.

Figure 9B:
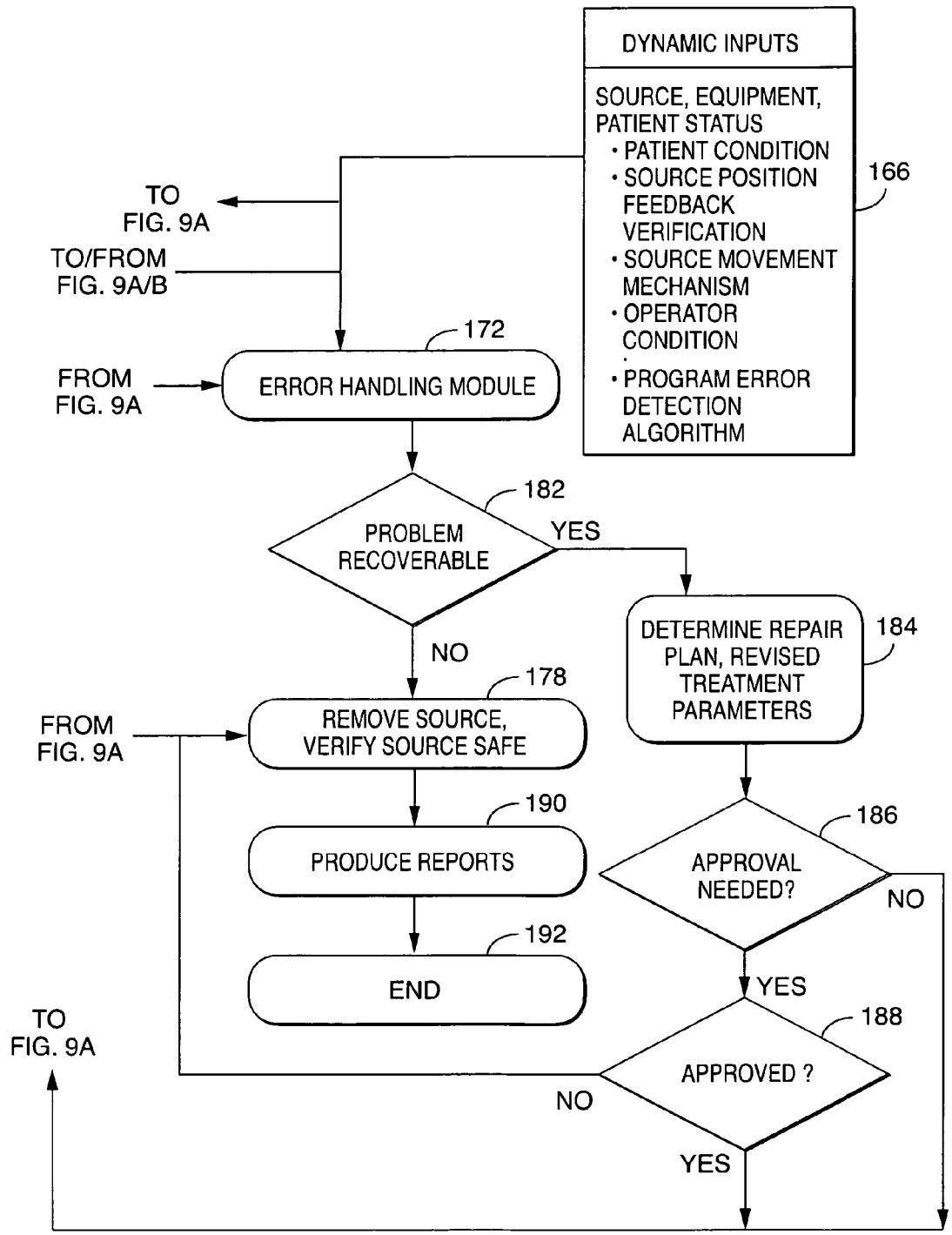

When treatment planning software, such as that described in connection with FIGS. 9A and 9B, the radiation exposure parameters such as isodose center, dose volume and dose uniformity are based on the size and shape of the breast or the size, shape and volume of the tumor, tumor bed, or a designated volume within the breast. Preferably, the radiation exposure parameters such as isodose center, dose volume and dose uniformity are designed to match the designated dose and dose distribution with the size and shape of the breast or the location and extent of the tumor or tumor bed within the breast, as identified from image guidance. The dose is preferably referenced to dose reference points within the breast identified from appropriate image guidance. The position, intensity, size, shape, energy of the source or sources are preferably chosen such that the radiation treatment volume coincides with the size and shape of the breast or the size, shape and location of the tumor, tumor bed or other designated volume within the breast based on image guidance. The dwell position, dwell pattern, and dwell time, of the HDR source is chosen such that the radiation treatment volume coincides with the size and shape of the breast or the size, shape and location of the tumor or tumor bed as identified by image guidance. For purposes of treatment, imagable markers within the applicators are used for alignment of the position of the applicator to the breast coordinates to coincide the radiation treatment volume to tumor or tumor bed volume. The treatment planning software preferably allows the dose to the treatment volume to be monitored in real-time so as to control the dwell position(s) and dwell time(s) of the source (s). The radioactive sources are encapsulated in a carrier which takes the shape of a point source, wire, tube, or foil, or may be loaded or embedded into a carrier by means of painting, plating, mixing into a dispersion, and chemical or physical bonding within or on the surface of a carrier. The sources can be small pellets or extended sources in the form of a line (one-dimensional). The sources can be filtered (shielded) or extended sources in the form of a flat plane (two-dimensional). The sources can be extended sources in the form of a curved plane (three dimensional). In one embodiment, the source(s) can traverse along a spiral trajectory along the periphery of the breast and extending from the chest wall to the nipple such as shown in FIGS. 3 and 4. In one alternative embodiment, the source(s) traverse multiple, co-axial circular trajectories, all of which are largely parallel to the chest wall and are located along the periphery of the breast. In yet another embodiment, the source(s) traverse along curved radial lines extending from nipple to the chest wall and are located along the periphery of the breast. The sources may be small pellets or extended sources in the form of a line (one-dimensional). The sources may be filtered (shielded) or extended sources in the form of a flat plane (two-dimensional). Or filtered (shielded) or extended sources in the form of a curved plane (three dimensional).

While certain embodiments have been described of an apparatus and method that provide brachytherapy, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for".

What is claimed:

1. A method of applying radiotherapy to a protruding organ, comprising:
   A. compressing the protruding organ between two plates so as to define an initial treatment plane;
   B. imaging the protruding organ in the initial treatment plane while it is immobilized to identify the designated volume of tissue in need of radiotherapy;
   C. delivering radiotherapy to the designated volume while the protruding organ is immobilized from a direction within an angle of 30 degrees from normal to the initial treatment plane;
   D. removing the compression plates and rotating the compression plates to a new orientation which is within 60 to 120 degrees of the initial treatment plane, and re-applying compression to immobilize the said protruding organ at the new orientation;
   E. identifying the designated volume by imaging, or other means, within the protruding organ from the new orientation; and
   F. delivering radiotherapy to the designated volume while the protruding organ is immobilized in the new orientation from a direction substantially normal to the compression plates.

2. The method according to claim 1, wherein the protruding organ is the breast.

3. The method according to claim 2, wherein the breast has been subjected to a lumpectomy procedure and wherein the designated volume is the lumpectomy cavity margin.

4. The method according to claim 1, wherein the steps A. B. and C. are performed with a single apparatus.

5. A method according to claim 1, further comprising:
   G. repeating steps D to F until a therapeutic dose is delivered to the designated volume within the protruding organ.

6. Apparatus according to claim 5, wherein removing the compression plates and rotating the compression plates to a new orientation defines a new treatment plane, and each dose is delivered from a direction within an angle of 30 degrees from normal to each treatment plane.

7. Apparatus according to claim 6, wherein the new treatment plane is within 60 to 120 degrees of the initial treatment plane.

8. An apparatus for applying radiotherapy to a protruding organ, comprising:
   A. a pair of plates constructed and arranged so as to rotate between at least (1) a first orientation so that the protruding organ can be compressed and immobilized so as to define an initial treatment plane, and (2) a second orientation different from the first orientation so that the protruding organ can be compressed and immobilized so as define a second treatment plane;
   B. an imaging device constructed and arranged so as to image the protruding organ while the organ is immobilized and so as to (a)identify a designated volume of the organ in need of radiotherapy in the first and second treatment planes; and
   C. a radiation delivery system constructed and arranged so as to deliver a dose of radiotherapy to the designated volume through the plates from at least two different directions while the protruding organ is immobilized in the first and second orientations.

9. The system according to claim 8, wherein the second treatment plane is within 60 to 120 degrees of the initial treatment plane.

10. The system according to claim 8, where the protruding organ is the breast.

11. The system according to claim 10, wherein the designated volume is defined by a lumpectomy cavity margin.

12. A system for applying non-invasive brachytherapy to a targeted volume within a conformable protruding organ of a patient, comprising:
   an applicator constructed so as to be positioned relative to the organ so that an enhanced dose of non-convergent radiation is deliverable from each of at least two locations at or very near the periphery of the conformable protruding organ transcutaneously to the targeted volume of the conformable protruding organ from at least two corresponding directions so that a higher dose is delivered to the targeted volume than to tissue surrounding the targeted volume;
   a control configured to include a treatment planning program used to guide the use of the applicator; and
   an image guidance device constructed and arranged so as image the targeted volume;
   wherein the treatment planning program and image guidance device are used to determine an optimum treatment plan, wherein the treatment planning program includes a parameter determination subprogram configured and arranged so as to determine radiation exposure parameters including isodose center, dose volume and dose uniformity as a function of the designated dose and dose distribution with the size and shape of the protruding organ and the location and extent of the targeted volume, as identified from the image guidance device.

13. A system according to claim 12, wherein the treatment planning program includes a subprogram configured and arranged so as to determine the position, intensity, size, shape, and energy of one or more sources for providing the enhanced dose as a function of the targeted volume, which in turn is determined by the size and shape of the organ, or the size and shape of the designated volume identified from the image guidance device.

14. A system according to claim 13, wherein the treatment planning program includes a subprogram configured and arranged so as to determine a dwell position, dwell pattern, and dwell time, of one or more sources for providing the enhanced dose coincides with the targeted volume.

15. A system according to claim 12, further including image markers arranged to align the position of the applicator to coordinates of the organ to coincide radiation treatment with the targeted volume.

16. A method of applying non-invasive brachytherapy to a targeted volume within a conformable protruding organ of a patient, comprising:
   positioning an applicator relative to the organ so that an enhanced dose of non-convergent radiation is deliverable from at least two locations at or very near the periphery of the conformable protruding organ transcutaneously to the targeted volume of the conformable protruding organ from at least two directions so that a higher dose is delivered to the targeted volume than to tissue surrounding the targeted volume;

using a treatment planning program to guide the use of the applicator;

using an image guidance device to image the targeted volume so as to determine the optimum treatment plan, wherein using the treatment planning program includes determining radiation exposure parameters including isodose center, dose volume and dose uniformity as a function of the designated dose and dose distribution with the size and shape of the protruding organ and the location and extent of the targeted volume, as identified from the image guidance device.

17. A method according to claim 16, wherein using the treatment planning program includes:

determining by the size and shape of the organ, and the size and shape of the designated volume identified from the image guidance device; and determining the position, intensity, size, shape, and energy of one or more sources for providing the enhanced dose as a function of the targeted volume.

18. A method according to claim 16, wherein using the treatment planning program includes determining the dwell position, dwell pattern, and dwell time, of one or more sources for providing the enhanced dose as it coincides with the targeted volume.

19. A method according to claim 16, further including using image markers arranged to align the position of the applicator to coordinates of the organ to coincide radiation treatment with the targeted volume.

\* \* \* \* \*